United States Patent [19]
Camus et al.

[11] Patent Number: 6,008,360
[45] Date of Patent: Dec. 28, 1999

[54] SUBSTITUTED 3-ARYL-3-CARBOXYALKYL GLUTARAMIDES, METHOD FOR PREPARING SAME BY 4-ARYLO-4-CYANOHEPTANE DICARBOXYLIC ACID CYCLISATION, AND USE THEREOF FOR PREPARING 3-ARYL-3-HYDROXYALKYLPIPERIDINES

[75] Inventors: Philippe Camus, Muret; Marcel Descamps, Le Lherm; Joël Radisson, Saubens, all of France

[73] Assignee: Sanofi-Synthelabo, Paris, France

[21] Appl. No.: 09/142,306

[22] PCT Filed: Mar. 5, 1997

[86] PCT No.: PCT/FR97/00388

§ 371 Date: Sep. 3, 1998

§ 102(e) Date: Sep. 3, 1998

[87] PCT Pub. No.: WO97/32852

PCT Pub. Date: Sep. 12, 1997

[30] Foreign Application Priority Data

Mar. 7, 1996 [FR] France ................... 96 02880

[51] Int. Cl.⁶ ............ C07D 213/22; C07D 409/00; C07D 411/00; C07D 211/40
[52] U.S. Cl. ............ 546/257; 546/280.4; 546/219; 546/220
[58] Field of Search ............ 546/219, 220, 546/257, 280.4

[56] References Cited

U.S. PATENT DOCUMENTS

| | | | |
|---|---|---|---|
| 3,379,731 | 4/1968 | Walker | 546/97 |
| 3,870,757 | 3/1975 | Kirchlechner et al. | 564/169 |
| 3,985,888 | 10/1976 | Carr et al. | |
| 5,340,822 | 8/1994 | Emonds-Alt et al. | 514/316 |
| 5,554,763 | 9/1996 | Emonds-Alt et al. | |
| 5,583,134 | 12/1996 | Emonds-Alt et al. | |
| 5,625,060 | 4/1997 | Emonds-Alt et al. | |

FOREIGN PATENT DOCUMENTS

| | | |
|---|---|---|
| 156433 | 10/1985 | European Pat. Off. |
| 512901 | 11/1992 | European Pat. Off. |
| 591040 | 4/1994 | European Pat. Off. |
| 673928 | 9/1995 | European Pat. Off. |

OTHER PUBLICATIONS

Fateen et al., Indian Journal of Chemistry, vol. 11, 1973, pp. 225–228.
Kaddah et al., Indian Journal of Chemistry, vol. 19B, 1980, pp. 122–124.
Jilek et al., Collect. Czech Chem. Commun., 36(9), 1971, pp. 3300–3313.
Chemical Abstracts No. 69–86577C (1968).
Koelsch, J. Org. Chem., vol. 25, 1960, pp. 164–174.
Branchini et al., Ann. Chim. vol. 51, 1961, pp. 1382–1391.
Derwent Patent Abstract of EP 673928 (Abstract No. 199543).
A.K. Fateen, Hydrolysis of some . . . , Indian Journal of Chemistry, vol. 11, pp. 225–228, XP 000609461, Jun. 1, 1972.
Rosanna Branchini et al , Derivati degli . . . XP 000607815, pp. 1382–1391, Sep. 18, 1961.
Fieser & Fieser , vol. 5 , pp. 184 and 185, May 1975.
Kaddah A.M. et al Indian Journal of Chemistry. RN#'s 61330–08–3p,75021–61–3, 75021–62–4, Sep. 26, 1979.
CA 1978 : 563376 , Fateen Abdel–Kader et al. Rev. Roum. Chim.

*Primary Examiner*—Alan L. Rotman
*Assistant Examiner*—Rita Desai
*Attorney, Agent, or Firm*—Michael D. Alexander

[57] ABSTRACT

The invention relates to glutarimides of formula (I):

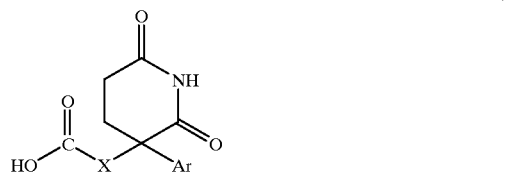

in which Ar represents a phenyl non substituted or substituted one or more times with one of the substitutents selected from a halogen atom, a hydroxyl, a ($C_1$–$C_4$)alkoxy, a trifluoromethyl, a ($C_1$–$C_4$)alkyl, said substitutents being identical or different ; a pyridyl group; a thienyl group and X is methylene or ethylene, their salts and their enantiomers, as well as their method of preparation and their use for the preparation of the corresponding 3,3-disubstituted piperidines.

19 Claims, No Drawings

SUBSTITUTED 3-ARYL-3-CARBOXYALKYL GLUTARAMIDES, METHOD FOR PREPARING SAME BY 4-ARYLO-4-CYANOHEPTANE DICARBOXYLIC ACID CYCLISATION, AND USE THEREOF FOR PREPARING 3-ARYL-3-HYDROXYALKYLPIPERIDINES

CROSS REFERENCE

This application is a 317 of PCT/FR97/00388 filed Mar. 5, 1997.

The present invention relates to novel glutarimides 3,3-disubstituted with an aryl group and a carboxy ($C_1$–$C_2$)alkyl group, a method for their preparation via novel intermediates and use of said glutarimides for the preparation of the corresponding piperidines, which are 3,3-disubstituted with the same aryl group and a hydroxy ($C_2$–$C_3$)alkyl group.

The EP 512 901 document describes antagonists of neurokinines which are prepared from piperidines which are 3,3-disubstituted with an aryl group and a hydroxyalkyl group. These 3,3-disubstituted piperidines are prepared from nitriles by reduction to the amines and cyclisation.

The publications of X. Edmonds-Alt et al., European Journ. Pharmacol., 1993, 250, 403–413 and Life Sciences 1995, 56 (1), 27–32 respectively describe an $NK_1$-antagonist, the chloride of (S)1-{2-[3-(3,4-dichlorophenyl)-1-(3-isopropoxyphenylacetyl)piperidin-3-yl]ethyl}-4-phenyl-1-azoniabicyclo[2.2.2]octane or SR 140333 and an $NK_3$-antagonist, (S)-N-[1-[3-{1-benzoyl-3-(3,4-dichlorophenyl)piperidin-3-yl}propyl]-4-phenylpiperidin-4-yl]-N-methylacetamide or SR 142801.

The preparation of these two products is described in EP 591 040 and EP 673 928, respectively. These documents describe 3,3-disubstituted piperidines as intermediates which can be represented by the following formula (A):

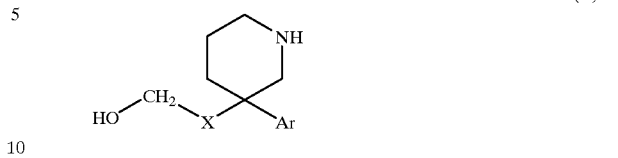

in which X is methylene or ethylene and Ar represents a phenyl non substituted or substituted one or more times with one of the substitutents selected from a halogen atom, a hydroxyl, a ($C_1$–$C_4$)alkoxy, a trifluoromethyl, a ($C_1$–$C_4$) alkyl, said substituents being identical or different; a pyridyl group; a thienyl group.

According to EP 512 901, EP 591 040 and EP 673 928, the preparation of the final products in optically pure form comprises the separation of the optical isomers of the compounds of formula (A) above.

In EP 673 928, the preparation of a 3,3-disubstituted piperidine of formula (A) in which X is ethylene and Ar is 3,4-dichlorophenyl is carried out from 3,4-dichlorophenylacetonitrile (i) by the action of methyl acrylate, cyclising methyl 4-cyano-4-(3,4-dichlorophenyl)-heptanedioate (ii) to give 3-(3,4-dichlorophenyl)-3-(2-methoxycarbonyl)ethyl-2-oxopiperidine (iii), saponifying this product in order to obtain the corresponding free acid (iv) and reducing the latter, according to the SCHEME A below.

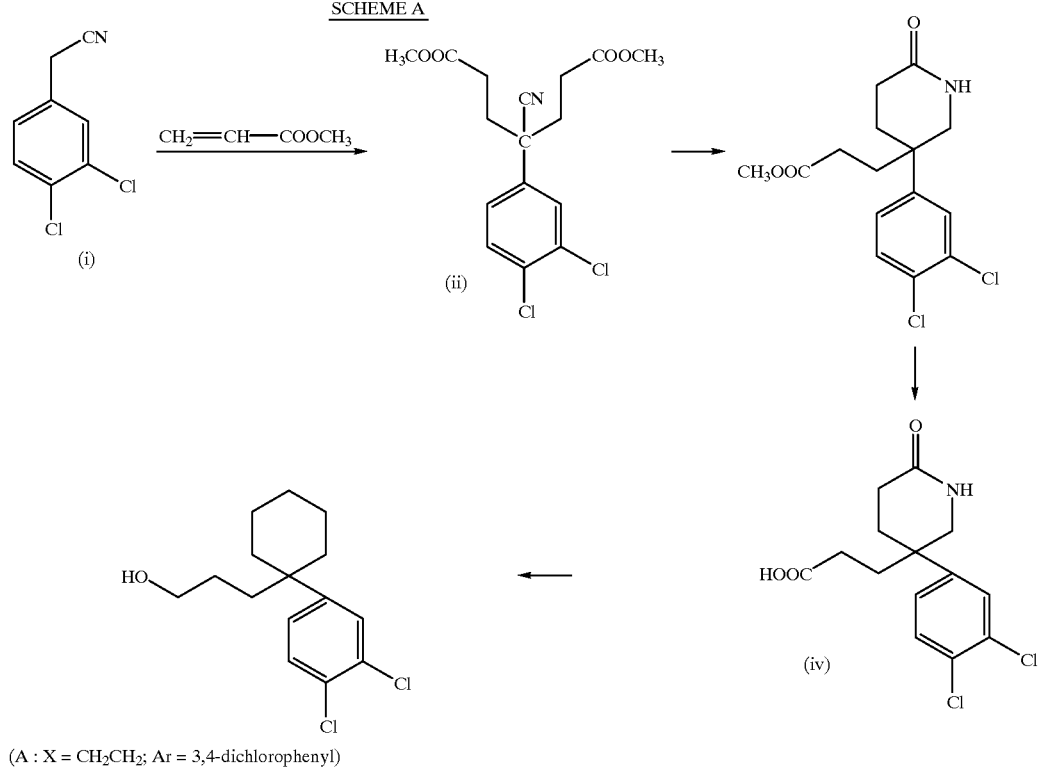

(A : X = CH₂CH₂; Ar = 3,4-dichlorophenyl)

It has now been found that in saponifying the compound (ii) above, the corresponding dicarboxylic acid is obtained which cyclises very easily with a very high yield giving a 3,3-disubstituted glutarimide.

It has also been found that this novel glutarimide can easily be resolved and converted into an optically pure compound of formula (A) by simple reduction.

It has also been found that, in the method of preparation of certain said glutarimides, it is possible to separate the optical isomers earlier when the intermediates possess an asymmetric carbon.

More generally, all a series of 3-carboxylalkyl-3-aryl-disubstituted glutarimides has been found which constitute useful intermediates for the preparation of 3,3-disubstituted piperidines of formula (A) above. Compared to the piperidine diones described in the WO94/21609 application, these 3,3-disubstituted glutarimides are interesting in that they may be resolved and used in the optically active form.

Thus, according to one of its aspects, the invention relates to a method of preparation of the glutarimides of formula (I):

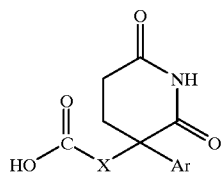
(I)

in which Ar represents a phenyl non substituted or substituted one or more times with one of the substituents selected from a halogen atom, a hydroxyl, a $(C_1-C_4)$alkoxy, a trifluoromethyl, a $(C_1-C_4)$alkyl, said substituents being identical or different; a pyridyl group; a thienyl group; and X is methylene or ethylene; and their salts and enantiomers, said method being, according to a first alternative, characterised in that:

a compound of formula (III):

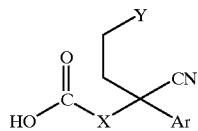
(III)

in which Ar and X ire such as defined above for the formula (I) and Y is a cyano or carboxy group is cyclised;

and the compound thus obtained of formula (I) is isolated in the form of one of its salts or in its acid form which is optionally converted into one of its salts.

When it is desired to prepare a glutarimide of formula (I) in which X is methylene, the starting compound of formula (III) possesses a chiral carbon atom. It is therefore possible to use an optically active compound as starting material. In this case, said starting product can have the formula (III), in which X is methylene and Y is cyano and may be optically active. Such a starting compound is particularly advantageous for the preparation of the glutarimides of formula (I), in which X is methylene, and of their salts.

The intermediate compounds of formula (III), in which X is methylene, Y is cyano and Ar is 3,4-difluorophenyl or 3,4-dichlorophenyl are preferred.

In an advantageous aspect of the method according to the invention, the compound of formula (III) is obtained by saponification of the ester group(s) of an α,α-disubstituted arylacetonitrile of formula (II):

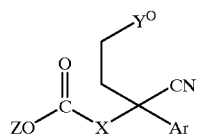
(II)

in which Ar and X are such as defined as above for the formula (I), $Y^O$ is a cyano or COOAlk group and Z is hydrogen or Alk, Alk being a $(C_1-C_3)$alkyl group.

The invention relates therefore, according to a second alternative, to a method of preparation of the glutarimides of formula (I) such as defined above, characterised in that:

(a) the ester group(s) of an α,α-disubstituted arylacetonitrile of formula (II):

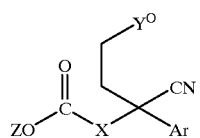
(II)

in which Ar and X are such as defined as above for the formula (I), $Y^O$ is a cyano or COOAlk group, Z is hydrogen or Alk, Alk being a $(C_1-C_3)$alkyl group, and at least one of the COOZ and $Y^O$ groups being COOAlk is (are) saponified;

(b) the compound of formula (III):

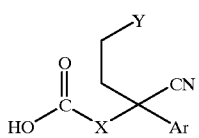
(III)

in which Ar and X are such as defined above and Y is a cyano or carboxy group is cyclised;

and the compound thus obtained of formula (I) is isolated in the form of one of its salts or in its acid form which is optionally converted into one of its salts.

According to this second alternative, when it is desired to prepare a glutarimide of formula (I) in which X is ethylene, which is the starting compound the most accessible, and therefore particularly advantageous, possesses the formula (II) in which X is ethylene, $Y^O$ is COOAlk and Z is Alk. In this case, the starting compound does not possess a chiral carbon atom.

The starting compounds of formula (II), in which X is ethylene, $Y^O$ is COOAlk and Z is Alk are particularly advantageous, those of formula (II) in which X is ethylene, $Y^O$ is $COOCH_3$, Z is $CH_3$ and Ar is 3,4-difluorophenyl or 3,4-dichlorophenyl are preferred.

The method according to the present invention (1st and 2nd alternatives) is illustrated in the SCHEME 1 below.

SCHEME 1

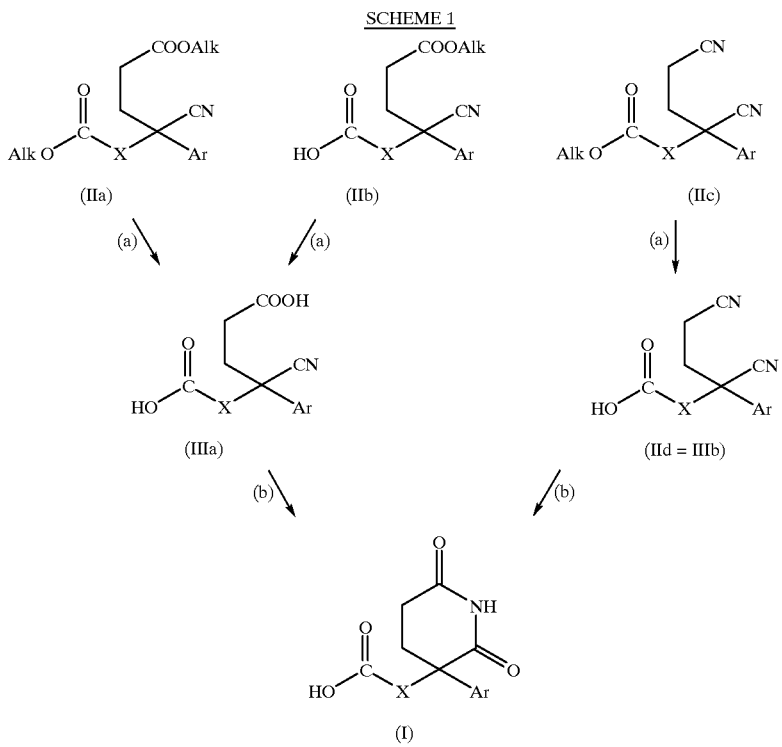

Step (a) of the method of the present invention (2nd alternative) consists of a saponification of the ester group present in the compound of formula (II), especially, according to SCHEME 1, the saponification of a compound selected from those represented by the formulae (IIa), (IIb) and (IIc).

The saponification is carried out preferably using an alkaline hydroxide or carbonate. The reaction takes place in an aqueous-alcohol medium or in a tetrahydrofuran/water mixture.

The compound of formula (III) is isolated by acidification with a mineral or organic acid such as sulphuric acid, hydrobromic acid, methanesulphonic acid or, preferably, hydrochloric acid to an acid pH value which can vary between 0 and 3, the pH at which the product precipitates.

In step (b) which characterises the 1st alternative of the method of the present invention, the cyclisation of the compound (III) is effected by a hydration in the presence of an acid selected from phosphoric acid, hydrochloric acid or preferentially with concentrated sulphuric acid. An aprotic solvent may also be used such as for example toluene, in this case in the presence of a sulphonic acid such as for example paratoluenesulphonic acid monohydrate or methanesulphonic acid in the presence of water. The reaction is conducted in a protic solvent such as for example in refluxing acetic acid. After 1 to 2 hours of heating, the reaction is complete and the glutarimide of formula (I) thus obtained is isolated according to the conventional methods. In general, it is sufficient to leave the reaction mixture to cool in order to separate the glutarimide off after precipitation or to pour the said reaction mixture into water in order to precipitate the final product out.

The glutarimide of formula (I) thus obtained can be isolated either in the form of the free acid directly from the reaction medium, or it may even be isolated in the form of one of its salts by treating the reaction mixture with the chosen base.

The free acid may also be converted into one of its salts, especially with an optically active organic base, so as to isolate a diastereoisomeric salt of the compound of formula (I) which, by neutralisation, gives one of the two enantiomers.

The method of the present invention, according to one or the other of its alternatives, also allows the separation of the optical isomers of certain intermediates (II) and (III), especially compounds having the formulae (IIb), (IIIa) and (IIIb), so as to effect this separation well upstream of the final product that one intends to obtain. The reactions which lead to the compound (I) do not however cause any racemisation.

This possibility confers a great advantage to the method of the present invention as compared to the known methods for the preparation of the 3,3-disubstituted piperidine of formula (A).

The starting compounds of formula (II) are either known or may be prepared according to known methods from an arylacetonitrile of formula $ArCH_2CN$.

In order to prepare the compounds of formula (II) in which X is methylene, the general method foresees the reaction of an arylacetonitrile of formula $ArCH_2CN$, in which Ar is such as defined above, with a haloacetic acid or one of its esters of formula (IV):

   (IV)

in which Z is such as defined above and Hal represents a halogen, preferably chlorine or bromine, or else by esterification of a cyanoacid of formula (V):

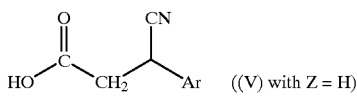   ((V) with Z = H)

in which Z represents hydrogen, under the conditions described in EP 612 716 for Ar equal to 3,4-dichlorophenyl. The product thus obtained, of formula (V):

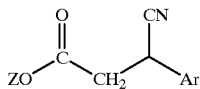 (V)

in which Z and Ar are such as defined above, is treated with an acrylic derivative of formula (VI):

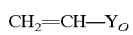 (VI)

in which $Y^O$ is such as defined above, under the well known conditions of acrylic condensation, in order to thus obtain the desired product.

Such a preparation with optional variants is illustrated in SCHEME 2 below.

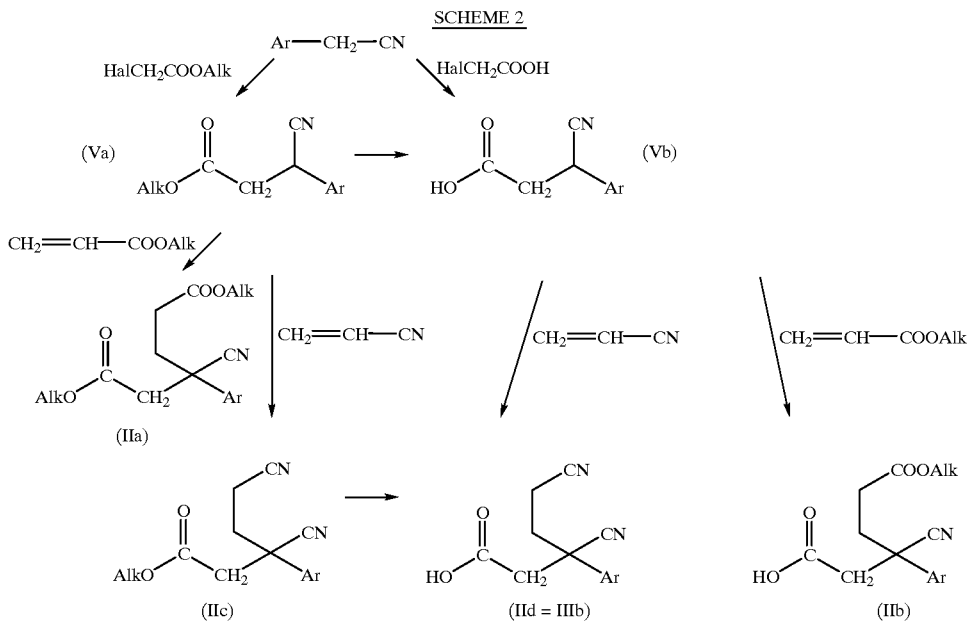

In order to prepare the compounds of formula (II) in which X is ethylene, the method illustrated in SCHEME 2 may be followed by using an alkyl β-halopropionate instead of the corresponding haloacetate.

It is however preferable to apply the acrylic condensation method directly on the arylacetonitrile of formula $ArCH_2CN$ by using a $(C_1-C_3)$alkyl acrylate, under the conditions described in EP 673 928 for Ar equal to 3,4-dichlorophenyl, according to the SCHEME 3 below.

The compound (IIb) above can also be obtained in the form of diacid by saponification of the corresponding ester.

The preparation of the ester (IIb) does not however lead to a primordial intermediate since the cyclisation giving the glutarimide is effected either from a nitrile function by reaction with an acid, or between two nitrile functions.

The compound (IIb) should therefore be saponified in every case.

The compound (IId), under the operating conditions used according to the present invention, leads preferentially to the cyclisation between the two nitrile functions, and therefore to the formation of the glutarimides and preferentially to that of the succinimide which would be the result of the cyclisation between the acid and nitrile functions.

SCHEME 3

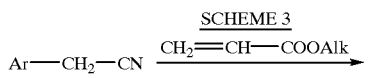

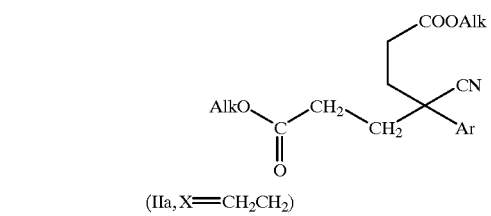

Consequently, according to the 2nd alternative of the method of the present invention, the preferential starting products are those of formula (IId) when X is methylene and those of formula (IIa) when X is ethylene.

The compounds of formula (III), which cyclise in excellent yields giving the glutarimides of the present invention, are the key intermediates in the method.

Amongst the compounds of formula (III), the compounds of formula (III'):

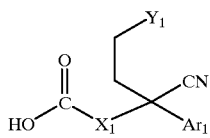

(III')

in which $Ar_1$ represents a phenyl non substituted or substituted one or many times with one of the substituents selected from a halogen atom, a hydroxyl, a $(C_1–C_4)$alkoxy, a trifluoromethyl, a $(C_1–C_4)$alkyl, said substituents being identical or different; a pyridyl group; a thienyl group, $X_1$ is methylene or ethylene, and $Y_1$ is a cyano or carboxy group, and their salts, provided that:

when $X_1$ is ethylene and $Y_1$ is a carboxy, $Ar_1$ is different from a non substituted phenyl or a phenyl substituted in position 3 with a methoxy, or 3,4-disubstituted with a methoxy, are novel products which constitute another aspect of the present invention.

The invention also concerns the compounds of formula (III''):

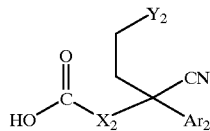

(III'')

in which $Ar_2$ represents a phenyl non substituted or substituted one or many times with one of the substituents selected from a halogen atom, a hydroxyl, a $(C_1–C_4)$alkoxy, a trifluoromethyl, a $(C_1–C_4)$alkyl, said substituents being identical or different; a pyridyl group; a thienyl group, $X_2$ is a methylene or ethylene, and $Y_2$ is a cyano or carboxy group, in the form of one of their optically active salts, one of their enantiomers or a salt thereof.

Amongst these compounds of formula (III') or (III''), those in which $Ar_1$ or $Ar_2$ is 3,4-difluorophenyl or 3,4-dichlorophenyl, as well as their salts, are particularly advantageous. The salts of these products with optically active amines are preferred. 3-(3,4-dichlorophenyl)-3,5-dicyanopentanoic acid and its salts with optically active amines, especially with 1-cinchonidine, are also very advantageous. (−)-3-(3,4-dichlorophenyl)-3,5-dicyanopentanoic acid is the key intermediate for the preparation of (−)-3-carboxymethyl-3-(3,4-dichlorophenyl)-2,6-dioxo-piperidine and therefore constitutes a particularly advantageous intermediate.

Another particularly advantageous intermediate, useful for the preparation of 3-carboxyethyl-3-(3,4.-dichlorophenyl)-2,6-dioxo-piperidine, is 4-cyano-4-(3,4-dichlorophenyl)-3,5-dicyanopentanoic acid, as it is or in the form of one of its salts.

Amongst the glutarimides of formula (I), the compounds of formula (I'):

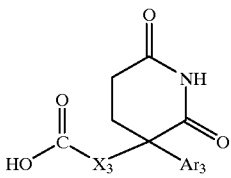

(I')

in which $Ar_3$ represents a phenyl non substituted or substituted one or more times with one of the substituents selected from a halogen atom, a hydroxyl, a $(C_1–C_4)$alkoxy, a trifluoromethyl, a $(C_1–C_4)$alkyl, said substituents being identical or different; a pyridyl group; a thienyl group and $X_3$ is methylene or ethylene and their salts, provided that:

when $X_3$ is methylene, $Ar_3$ is different from a non substituted phenyl; and when $X_3$ is ethylene, $Ar_3$ is different from a non substituted phenyl or a phenyl substituted in position 2 with a methyl or in position 4 with a chlorine atom, a fluorine atom, a bromine atom, a methyl or a methoxy, are novel products which constitute another aspect of the invention.

The invention also relates to the glutarimides of formula (I'')

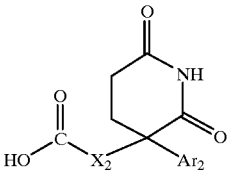

(I'')

in which $Ar_2$ and $X_2$ are such as defined above for the formula (III''), in the form of one of its optically active salts, one of its enantiomers or one of the salts thereof.

The preferred glutarimides according to the present invention are those of formula (I') or (I'') above, in which X is methylene or ethylene and $Ar_3$ or $Ar_2$, if need be, is 3,4-dichlorophenyl or 3,4-difluorophenyl, their salts and their enantiomers.

The salts of the glutarimides of formula (I') or (I'') may be those with inorganic or organic bases, for example the salts of sodium, potassium, calcium, magnesium, barium, zinc, silver, trimethylamine, triethylamine, tris-hydroxymethylmethanamine (tromethanol), ethanolamine, diethanolamine, 1-methylpiperidine, 4-methylmorpholine or an optically active base, particularly an optically active amine.

Particularly preferred are the salts of the glutarimides of formula (I') or (I''), in which X is methylene or ethylene and $Ar_3$ or $Ar_2$, if need be, is 3,4-difluorophenyl or 3,4-dichlorophenyl, with optically active amines.

The glutarimides of formula (I) as well as their salts, especially those with optically active amines, are useful for the preparation of the 3,3-disubstituted piperidines of formula (A).

When the said glutarimides are in the optically active form, they are useful for the preparation of the corresponding optically active 3,3-disubstituted piperidines of formula (A), since the transformation does not cause racemisation.

Therefore, an object of the present invention consists, according to another of its aspects, of the use of the glutarimides of formula (I):

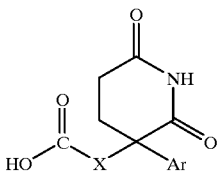

(I)

in which Ar represents a phenyl non substituted or substituted one or many times with one of the substituents selected from a halogen atom, a hydroxyl, a $(C_1-C_4)$alkoxy, a trifluoromethyl, a $(C_1-C_4)$alkyl, said substituents being identical or different; a pyridyl group; a thienyl group; and X is methylene or ethylene, of its salts and enantiomers, for the preparation of 3,3-disubstituted piperidines of formula (A) and their salts.

Said preparation takes place by reduction of the glutarimides, during which both carbonyl groups of the glutarimide and the carbonyl group of the carboxylic acid are converted into the corresponding methylene groups at the same time.

Thus, another aspect of the present invention consists to provide a method for the preparation of 3,3-disubstituted piperidines of formula (A) and their salts with inorganic or organic acids, characterised in that a corresponding glutarimide of formula (I) such as defined above is submitted to reduction, and said piperidine is isolated in the form of a base or one of its salts, or the free base is converted into one of its salts.

The reducing agents used are borane complexes such as for example borane-tetrahydrofuran or borane-dimethylsulphide or even a mixed alkaline hydride such as lithium aluminium hydride or sodium bis(2-methoxyethoxy)aluminium hydride in solution in toluene (Red-Al®). These reductions take place without racemisation, the preferred reducing agent is a borane complex.

The reduction with borane is carried out in a solvent preferably aprotic such as tetrahydrofuran at the reflux temperature of the solvent. In general, after 1 to 16 hours of heating, the reduction is complete and the 3,3-disubstituted piperidine is isolated, according to the conventional methods, in first destroying the excess of borane with methanol. The free base can be isolated by evaporating the solvent, taking the residue up into water, acidifying with hydrochloric acid, treating with a base, preferably sodium hydroxide, and extracting with a solvent.

The free base of formula (A) can be transformed into one of its salts according to well-known techniques. The borane used for the reduction can be generated in situ according to the conventional methods.

The glutarimide of formula (I) used for the preparation of the corresponding 3,3-disubstituted piperidine of formula (A) can be in the racemic form or in the optically active form.

When the glutarimide has the formula (I) in which X is ethylene and that it is prepared according to the preferential route by cyclisation of the diacid (IIIa), it does not possess a chiral carbon and, consequently, said glutarimide is inevitably racemic. In this case, the separation of the optical isomers can be effected either on the glutarimide, or on the 3,3-disubstituted piperidine. In any case, the reduction with borane is practically quantitative and the operator can select one of the two alternatives with the same result in terms of yields.

Furthermore, the saponification of the ester (IIa) (X=ethylene) and the cyclisation of the diacid (IIIa) (X=ethylene) take place with excellent yields, rendering the method of the present invention particularly advantageous compared to that described in EP 673 928.

The following examples illustrate the invention.

The melting points have been measured on a Tottoli apparatus.

The chemical shifts in the NMR spectra are expressed in ppm.

PREPARATION I—COMPOUND (IIa)

Methyl 4-Cyano-4-(3,4-dichlorophenyl)heptanedioate

Compound (IIa.1)

To a solution of 187 g of 3,4-dichlorophenylacetonitrile in 250 ml of tetrahydrofuran under reflux containing 4 ml of Triton B are added progressively 175 g of methyl acrylate and heating is continued for 30 minutes under reflux. After reaction, the tetrahydrofuran is distilled off, the concentrate is redissolved in 1 litre of toluene and the solution is washed with 400 ml of dilute hydrochloric acid and then with 2×150 ml of water. The toluene is distilled off and the residue is crystallised in 500 ml of cyclohexane. The expected product is filtered, rinsed with cyclohexane and dried at 45° C. in a ventilated oven to provide 340 g of the expected diester; yield 95%; M. Pt.=84–85° C. (formula (IIa), X=$CH_2CH_2$, Alk=$CH_3$, Ar=3,4-dichlorophenyl).

$^1$H NMR 200 MHz, DMSO: 2,30 (s, 6H); 3,50 (s, 6H); 2,08 (m, 2H); 7,4 (Ar, 1H); 7,7 (Ar, 2H).

By replacing methyl acrylate with equimolecular amounts of ethyl acrylate and propyl acrylate, it is possible to obtain:

ethyl 4-cyano-4-(3,4-dichlorophenyl)heptanedioate, Compound (IIa.2) and, respectively, propyl 4-cyano-4-(3,4-dichlorophenyl)heptanedioate, Compound (IIa.3).

PREPARATION II—COMPOUND (IIa)

Methyl 4-Cyano-4-(3,4-difluorophenyl)heptanedioate,

Compound (IIa.4)

In performing as described in PREPARATION I, and by replacing 3,4-dichlorophenylacetonitrile with 3,4-difluorophenylacetonitrile, methyl 4-cyano-4-(3,4-difluorophenyl)heptanedioate (formula (IIa), X=$CH_2CH_2$, Alk=$CH_3$, Ar=3,4-difluorophenyl) is obtained.

In the same manner, by replacing methyl acrylate with ethyl acrylate or propyl acrylate, it is possible to obtain, respectively:

ethyl 4-cyano-4-(3,4-difluorophenyl)heptanedioate, Compound (IIa.5)

isopropyl 4-cyano-4-(3,4-difluorophenyl)heptanedioate, Compound (IIa.6)

PREPARATION III—COMPOUND (IIa)

In performing as described in PREPARATION I, starting with 3-pyridineacetonitrile, 2-thienylacetonitrile or 3-thienylacetonitrile, it is possible to obtain:

methyl 4-cyano-4-(3-pyridyl)heptanedioate, Compound (IIa.7)

methyl 4-cyano-4-(2-thienyl)heptanedioate, Compound (IIa.8)

methyl 4-cyano-4-(3-thienyl)heptanedioate, Compound (IIa.9).

PREPARATION IV—COMPOUND (IIa)

3-Cyano-3-,(3,4-dichlorophenyl)propionic acid, Compound (IIa.10)

109 g of 3,4-dichlorophenylacetonitrile dissolved in 300 ml of tetrahydrofuran are introduced, under nitrogen at 20° C., into a round-bottomed flask. 240 ml of lithium diisopropylamide (2M) are then poured at −10° C. Once the addition is complete, 68 g of sodium chloroacetate are introduced, at the temperature of 15° C. The reaction mixture is stirred for three hours and then 350 ml of tert-butylmethylether are added. The reaction mixture is then poured into 300 ml of water and 150 g of ammonium sulphate as well as 400 ml of water and 175 g of ammonium bisulphate. The aqueous phase is removed and the organic phase is successively washed with water, dried and concentrated in vacuo in order to provide the cyanoacid; Yield 93%.

PREPARATION V—COMPOUND (IIa)

Methyl 3-Cyano-3-(3,4-dichlorophenyl)propionate (a) 320 g of potassium carbonate are added to a solution of 260 g of 3-cyano-3-(3,4-dichlorophenyl) propionic acid in 2.7 litres of acetonitrile. The suspension is heated under reflux in adding progressively 110 ml of dimethylsulphate. The mixture is left to return to room temperature after 15 minutes. The reaction mixture is concentrated and then taken up into 2 litres of dichloromethane. The organic phase is washed with water and then concentrated. The residue is taken up into 500 ml of methanol in order to provide the expected ester with a yield of 80%.

Methyl 3-Cyano-3-(3,4-dichlorophenyl) hexanedioate, Compound (IIa.11)

(b) 7 ml of Triton B are added to a solution of 20 g of the cyanoester, prepared previously according to PREPARATION IV, in 100 ml of tetrahydrofuran. 20 ml of ethyl acrylate are added to the reaction mixture at 66° C. over 30 minutes. The reaction mixture is concentrated, taken up into 60 ml of dichloromethane and washed with three times 60 ml of water. The cyanodiester is isolated by crystallisation in 80 ml of methanol. (Formula (IIa), X=$CH_2$, Alk=$CH_3$, Ar=3,4-dichlorophenyl).

PREPARATION VI—COMPOUND (IIa)

(a) Methyl 3-Cyano-3-(3,4-difluorophenyl) propionate

In performing as described in PREPARATION IV from 3,4-difluorophenyl-acetonitrile, methyl 3-cyano-3-(3,4-difluorophenyl) propionate is obtained.

(b) Methyl 3-Cyano-3-(3,4-difluorophenyl) hexanedioate Compound (IIa.11)

Methyl 3-cyano-3-(3,4-difluorophenyl)hexanedioate can be obtained from methyl 3-cyano-3-(3,4-difluorophenyl) propionate obtained in step (a) by reaction with methyl acrylate under the same conditions as those of PREPARATION V(b).

EXAMPLE 1

(a) 4-Cyano,-4-(3,4-dichlorophenyl)heptanedioic acid

From a Diester 358.2 g of the diester obtained in PREPARATION I and 1.5 litres of methanol are introduced into a round-bottomed flask. 250 ml of 30% sodium hydroxide and 100 ml of water are then added. The mixture becomes limpid and is left to stir for 1 hour and 30 minutes at room temperature until the ester has disappeared. The methanol is then evaporated in vacuo and an oily residue is obtained which is taken up into 1.5 litres of water, then successively cooled in an ice-bath and acidified with the aid of sulphuric acid until white crystals precipitate at pH<3. The diacid is separated off by filtration, sucked dry and rinsed with water (pH=5) and then dried to constant weight in a ventilated oven in order to provide 326 g of the expected product.

From a Nitrile 175 g of methyl acrylate are progressively added to a boiling solution of 187 g of 3,4-dichlorophenylicetonitrile in 250 ml of tetrahydrofuran containing 4 ml of Triton B. Heating is continued for 30 minutes under reflux. After reaction, the tetrahydrofuran is distilled off, the residue is dissolved in 1.5 litres of methanol and a 30% sodium hydroxide solution is added. The reaction mixture is stirred for 1 hour at room temperature until the ester has disappeared, and then the methanol is distilled off. The residue is dissolved in 1.5 litres of water, acidified to pH<3 with dilute sulphuric acid and left to crystallise for 30 minutes. The diacid is filtered, rinsed with water to neutrality (pH 5) and dried in a ventilated oven to constant weight at 60° C. in order to provide 314 g of expected product; Yield: 95%. (Formula (IIIa), X=$CH_2CH_2$, Ar=3,4-dichlorophenyl)

$^1$H NMR 200 MHz, DMSO: 2,0 (m, 2H); 2,29 (s, 6H); 7,4 (Ar, 1H); 7,65 (Ar, 2H); 11,5 (COOH, 2H).

(b) Racemic 3-(2-Carboxyethyl)-3-(3,4-dichlorophenyl)-2,6-dioxo-piperidine 330 g of 4-cyano-4-(3,4-dichlorophenyl) heptanedicarboxylic acid obtained previously are heated under reflux for 30 minutes in 1 litre of acetic acid containing 50 g of concentrated sulphiric acid. After reaction, the reaction mixture is left to crystallise and the expected product is filtered off, rinsed with acetic acid and then with t-butylmethylether until Congo paper no longer turns blue (pH>3). The product is dried to constant weight in a ventilated oven at 70° C. in order to provide 306.5 g of the expected product; Yield=92%; M.Pt.=234° C.

$^1$H NMR 200 MHz, DMSO: 2,0 and 2,5 (m, 8H); 7,25 (Ar, 1H); 7,5–7,6 (Ar, 2H); 11,0 (s, NH); 12 (COOH, 1H).

EXAMPLE 2

Quinine salt of (+)-3-(2-carboxyethyl)-3-(3,4-dichlorophenyl)-2,6-dioxopiperidine 65.4 g of quinine in solution in 1 litre of methanol are added to 100 g of the racemic compound prepared previously dissolved in 1 litre of 0.5 M ammonia solution. The product which has crystallised is filtered off and washed with a 75/25 water/methanol mixture and then recrystallised from a 50/50 methanol/water mixture. 78.7 g of the quinine salt of (+) 3-(2-carboxyethyl)-3-(3,4-dichlorophenyl)-2,6-dioxopiperidine are obtained after drying, enantiomeric purity 97% determined by HPLC after derivatisation with (S)-methylbenzylamine.

EXAMPLE 3

(+)-3-(2-Carboxyethyl)-3-(3,4-dichlorophenyl)-2,6-dioxopiperidine 70 g of the quinine salt obtained according to EXAMPLE 2 are dissolved in a mixture of 1.3 litres of ethyl acetate and 1.3 litres of 1N hydrochloric acid. The aqueous phase is discarded, the organic phase is dried over sodium sulphate and concentrated to dryness. The residue is crystallised in 200 ml of petroleum ether and dried at 40° C. M.Pt.=201° C.

$[\alpha]_D^{20}$=+137.1 (c=1, $CH_3OH$)

EXAMPLE 4

(a) 4-cyano-4-(3,4-difluorophenyl)heptanedioic acid

By saponification of the methyl diester obtained in PREPARATION II and according to the conditions described in EXAMPLE 1(a), 4-cyano4-(3,4-difluorophenyl)heptanedioic acid may be obtained (Formula (IIIa), X=$CH_2CH_2$, Ar=3,4-difluorophenyl).

(b) 3-(2-Carboxyethyl)-3-(3,4-difluorophenyl)-2,6-dioxopiperidine

The cyclisalion of the diacid obtained in step (a), by dehydration with 80% sulphuric acid in acetic acid under the conditions of EXAMPLE 1(b), provides the expected product (Formula I, X=$CH_2CH_2$, Ar=3,4-difluorophenyl).

EXAMPLE 5

(a) 3,5-dicyano-3-(3,4-dichlorophenyl)pentanoic acid

A solution of 122 g of the cyanoacid prepared previously in dichloromethane is introduced into a round bottomed flask. 500 ml of a 2N solution of sodium hydroxide are then added dropwise in maintaining the temperature at 15° C. Once the addition is complete, the organic phase is left to decant and is then separated off. The organic phase is then poured into a round-bottomed flask, and 50 ml of acrylonitrile are then added with stirring over 30 minutes whilst keeping the temperature below 20° C., 5 ml of acrylonitrile are then added. The reaction mixture is stirred for thirty minutes and then cooled to 10° C. 500 ml of 2N hydrochloric acid are then added dropwise. The mixture is then left to stir, and then the precipitate is separated off by filtration, which after rinsing with water and drying, provides 121 g of the expected dinitrile (Formula (IIIb) or (IId), X=$CH_2$, Ar=3,4-dichlorophenyl); M. Pt.=170° C.

(b) 3-Carboxymethyl-3-(3,4-dichlorophenyl)-2,6-dioxopiperidine 20 g of the derivative prepared according to (a) in 80 ml of acetic acid are introduced into a round-bottomed flask. 6.75 ml of 80% sulphuric acid are then added dropwise and the reaction mixture is heated to 80° C. and then under reflux for 1 hour and 30 minutes. The reaction mixture is then left to return to room temperature and 240 ml of iced water are added to it. After stirring at 10° C. for 30 minutes, the precipitate is separated off by filtration. The precipitate is taken up into 130 ml of acetic acid which is then distilled off in order to obtain a residue which crystallises providing 17 g of the expected product (Formula (I), X=$CH_2$, Ar=3,4-dichlorophenyl); M. Pt.=203° C.

EXAMPLE 6

Cinchonidine salt of (−)-3,5-dicyano-3-(3,4-dichlorophenyl) pentanoic acid 50 g of the product of EXAMPLE 3(a) in 375 ml of methanol are introduced into a three necked flask equipped with mechanical stirring. 24.8 g of 1-cinchonidine are then added and the reaction mixture is heated under reflux for one hour. It is then left to cool and a precipitate is separated off by filtration which, after drying, provides 31.1 g of the expected product (Formula (III), X=$CH_2$, Y=COOH, Ar=3,4-dichlorophenyl, (−) isomer); M. Pt.=199.5° C.

EXAMPLE 7

(−)-3,5-Dicyano-3-(3,4-dichlorophenyl)pentanoic acid 15 g of the cinchonidine salt prepared previously are placed in suspension in 75 ml of water with mechanical stirring in a three necked flask. 9.5 ml of 6N hydrochloric acid are then added cropwise in maintaining the temperature of the reaction mixture at 20° C. in an ice-bath whilst stirring for 30 minutes. The precipitate is separated off by filtration which is then rinsed with water and dried in vacuo in order to provide 7.96 g of the expected compound (Formula (IIIb), X=$CH_2$, Ar=3,4-dichlorophenyl, (−) isomer);

$[\alpha]_D^{20}$=−2 (c=1, $CH_3OH$)

(+) Enantiomer:

$[\alpha]_D^{20}$=+2 (c=1, $CH_3OH$)

EXAMPLE 8

(+)-3-Carboxymethyl-3-(3,4-dichlorophenyl)-2,6-dioxopiperidine

In proceeding according to EXAMPLE 5(b) from the acid obtained in EXAMPLE 7, the above optically pure compound is obtained, M. Pt.=229° C.

$[\alpha]_D^{20}$=+131,5 (c=1, $CH_3OH$)

(−) Enantiomer:

$[\alpha]_D^{20}$=−131,5 (c=1, $CH_3OH$)

EXAMPLE 9

(a) 3-cyano-3-(3,4-dichlorophenyl)hexanedioic acid

To a suspension of 11 g of the cyanodiacid prepared previously according to EXAMPLE 7, in 34 ml of methanol, is added 33 ml of 4N sodium hydroxide. After 30 minutes at 40° C., the reaction mixture is concentrated, taken up into 42 ml of water and acidified with hydrochloric acid to a pH<3. The expected acid precipitates from the aqueous phase. After filtration and drying, 9.9 g of the expected compound are isolated; M. Pt.=152° C.; Yield 98%.

(Formula (IIIa), X=$CH_2$, Ar=3,4-dichlorophenyl).

(b) 3-Carboxymethyl-3-(3,4-dichlorophenyl)-2,6-dioxopiperidine

From the diacid obtained in step (a), by cyclisation under the conditions described in EXAMPLE 1(b), the expected product is obtained, identical to that of EXAMPLE 5(b).

EXAMPLE 10

Utilisation of 3-carboxymethyl-3-(3,4-dichlorophenyl)-2,6-dioxopiperidine for the preparation of 3-(,3,4-dichlorophenyl)-3-(2-hydroxy-ethyl)piperidine 58.0 g of the compound prepared previously in 600 ml of tetrahydrofuran are introduced into a round-bottomed flask equipped with a mechanical stirrer. 800 ml of a 1.0 M solution of borane in tetrahydrofuran are then slowly added dropwise. The reaction mixture is then heated in stages upto reflux for 5 hours. The temperature is then left to return to room temperature, and 300 ml of methanol are then added slowly. The reaction mixture is then concentrated in vacuo in order to provide a residue which is taken up into water and then successively, the aqueous phase is acidified with a 35% solution of hydrochloric acid, heated under reflux with stirring for 1 hour and brought back to room temperature. A basification is carried out to pH=14 by the addition of a concentrated sodium hydroxide solution and then an extraction with 400 ml of dichloromethane. The organic phases are combined and then successively washed with water, dried over $Na_2SO_4$, filtered and concentrated in vacuo in order to provide a residue which, after drying, leads to 46.4 g of the expected product (Formula A, X=$CH_2$, Ar=3,4-dichlorophenyl); M. Pt.=122° C.

EXAMPLE 11

Use of (+)-3-(2-carboxyethyl)-3-(3,4-dichlorophenyl)-2,6-dioxopiperidine for the preparation of (+)-3-(3,4-dichlorophenyl)-3-(3-hydroxypropyl) piperidine 110 ml of a 1 M solution of borane in tetrahydrofuran are added to 33.0 g of the product prepared previously according to EXAMPLE 3 in 120 ml of tetrahydrofuran between 0 and 20° C. When the exothermicity has stopped, the reaction mixture is heated to 40° C., and then 340 ml of 1 M borane in tetrahydrofuran are added and the mixture is heated for 2 hours under reflux. The excess borane is destroyed by the progressive addition of 100 ml of methanol. The reaction mixture is concentrated to dryness, 400 ml of 6 M hydrochloric acid are added and the mixture is heated for 30 minutes under reflux. After returning to room temperature, the mixture is basified to pH 14 with a solution of sodium hydroxide and extracted with 200 ml of butanol. The organic phase is washed with water, concentrated to the maximum in vacuo, taken up into toluene and again concentrated to dryness in vacuo. The concentrate is taken up into dichloromethane, anhydrous hydrogen chloride is added, and is evaporated to dryness and solidified in acetonitrile in order to provide 26.2 g of the expected product (Formula A, X=$CH_2CH_2$, Ar=3,4-dichlorophenyl).

$[\alpha]_D^{20}$=+6,5 (c=1, $CH_3OH$)

The camphorsulphonate of this derivative is also prepared by reaction with camphorsulphonic acid;

$[\alpha]_D^{20}$=+23,0 (c=1, $CH_3OH$)

We claim:
1. A method for the preparation of a glutarimide of formula (I):

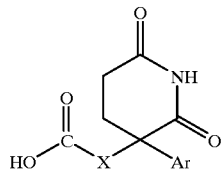

(I)

in which Ar represents a phenyl non substituted or substituted one or more times with one of the substituents selected from a halogen atom, a hydroxyl, a ($C_1$–$C_4$)alkoxy, a trifluoromethyl, a ($C_1$–$C_4$)alkyl, said substituents being identical or different; a pyridyl group; a thienyl group and X is methylene or ethylene, of its salts and of its enantiomers, wherein:

a compound of formula (III):

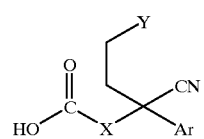

(III)

in which Ar and X are such as defined in claim 1 and Y is a cyano or carboxy group is cyclised; and the compound thus obtained of formula (I) is isolated in the form of one of its salts or its acid form which is optionally converted into one of its salts.

2. A method for the preparation of a glutarimide of formula (I):

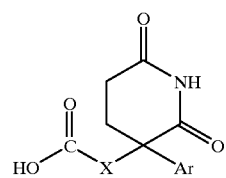

(I)

in which Ar and X are such as defined in claim 1, of its salts and of its enantiomers, wherein:

(a) the ester group(s) of an α,α-disubstituted arylacetonitrile of formula (II):

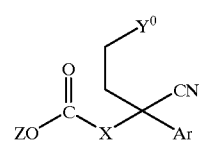

(II)

in which Ar and X are such as defined in claim 1, $Y^°$ is a cyano or COOAlk group, Z is hydrogen or Alk, Alk being a ($C_1$–$C_3$)alkyl group, and at least one of the COOZ and $Y^°$ groups being COOAlk is (are) saponified., (b) the compound of formula (III) is cyclised:

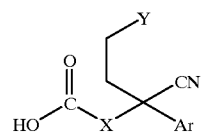

(III)

in which Ar and X are such as defined above and Y is a cyano or carboxy group is cyclised; and the compound thus obtained is isolated in the form of one of its salts or in its acid form which is optionally converted into one of its salts.

3. A method according to claim 1, wherein a compound of formula (III) is used as starting product in which X, Y and Z, are such as defined in claim 1 and Ar represents 3,4-difluorophenyl or 3,4-dichlorophenyl.

4. A method according to claim 2, wherein a compound of formula (II) is used as starting product in which X, Y°, and Z are such as defined in claim 2 and Ar represents 3,4-difluorophenyl or 3,4-dichlorophenyl.

5. A method according to claim 2, wherein a compound of formula (II) is used as starting product in which X is ethylene, Y° is COOAlk and Z is Alk, Alk being ($C_1$–$C_3$) alkyl and the starting compound of step (b) has the formula (III) in which X is ethylene and Y is carboxy.

6. A method according to claim 5, wherein methyl 4-cyano-4-(3,4-dichlorophenyl)heptanedioate is used as starting product.

7. A method according to claim 1, wherein a compound of formula (III) is used as starting product in which X is methylene, Y is cyano and Ar is such as defined in claim 1.

8. A method according to claim 2, wherein 3-(3,4-dichlorophenyl)-3,5-dicyanopentanoic acid is used as starting product either in the racemic form, or in the (−) form.

9. A glutarimide of formula (I'):

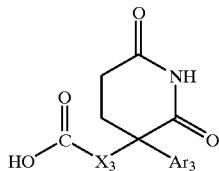

(I')

in which $Ar_3$ represents a phenyl substituted one or more times with one of the substituents selected from a halogen atom, a hydroxyl, a ($C_1$–$C_4$) alkoxy, a trifluoromethyl, a ($C_1$–$C_4$)alkyl, said substituents being identical or different; a pyridyl group; a thienyl group and $X_3$ is methylene or ethylene, and its salts, provided that:

when $X_3$ is ethylene, $Ar_3$ is different from a phenyl substituted in position 2 with a methyl or in position 4 with a chlorine atom, a fluorine atom, a bromine atom, a methyl or a methoxy.

10. A glutarimide of formula (I"):

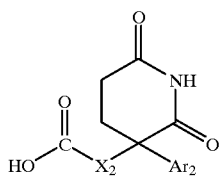

(I")

in which $Ar_2$ represents a phenyl non substituted or substituted one or more times with one of the substituents selected from a halogen atom, a hydroxyl, a ($C_1$–$C_4$)alkoxy, a trifluoromethyl, a ($C_1$–$C_4$)alkyl, said substituents being identical or different; a pyridyl group; a thienyl group and $X_2$ is methylene or ethylene, in the form of one of its optically active salts, one of its enantiomers, or a salt thereof.

11. A glutarimide according to claim 9 wherein in the formula (I) $Ar_3$ is 3,4-difluorophenyl or 3,4-dichlorophenyl.

12. A glutarimide according to claim 9 in the form of one of its salts with optically active amines.

13. A method for the preparation of a 3,3-disubstituted piperidine of formula (A):

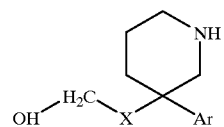

(A)

in which Ar and X are such as defined in claim 1, and of its salts with inorganic or organic acids, wherein a glutarimide of formula (I):

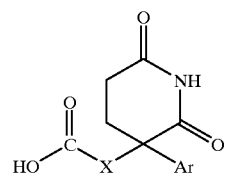

(I)

is submitted to a reduction action using a reducing agent selected from borane-tetrahydrofuran, borine-dimethylsulfide, lithium aluminum hydride, and sodium bis (2-methoxyethoxy)aluminum hydride and said 3,3-disubstituted piperidine is isolated in the form of a base or one of its salts or the free base is converted is converted into one of its salts.

14. A method according to claim 13, wherein the reduction reaction is carried out with borane.

15. A method according to claim 14 wherein a glutarimide of formula (I):

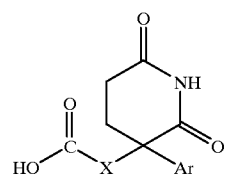

(I)

in which Ar represents a phenyl substituted one or more times with one of the substitutuents selected from a hydroxyl, a ($C_1$–$C_4$) alkoxy, a trifluoromethyl, a ($C_1$–$C_4$) alkyl, said substituent being identical or different; a pyridyl group; a thienyl group and X is methylene or ethylene is used as a starting compound.

16. A glutarimide according to claim 10 wherein in the formula (I) $Ar_2$ is 3,4-difluorophenyl or 3,4-dichlorophenyl.

17. A glutarimide according to claim 10 in the form of one of its salts with optically active amines.

18. A glutarimide according to claim 11 in the form of one of its salts with optically active amines.

19. A glutarimide according to claim 16 in the form of one of its salts with optically active amines.

* * * * *